United States Patent [19]

Kökosi et al.

[11] 4,367,229
[45] Jan. 4, 1983

[54] 3-SUBSTITUTED-TETRAHYDRO-PYR-ROLO[1,2-a]PYRIMIDINES AND PHARMACEUTICAL COMPOSITIONS

[75] Inventors: József Kökosi, Budaörs; István Hermecz, Budapest; Zoltán Mészáros, Budapest; György Szász, Budapest; Lelle Vasuárl née Debreczy, Budapest; Ágnes Horváth, Budapest; Tibor Breining, Budapest, all of Hungary

[73] Assignee: Chinoin Gyogyszer es Vegyeszeti Termekek Gyara Rt., Budapest, Hungary

[21] Appl. No.: 148,239

[22] Filed: May 9, 1980

[30] Foreign Application Priority Data

May 11, 1979 [HU] Hungary ............................. CI 1930

[51] Int. Cl.³ ................. C07D 487/04; A61K 31/505
[52] U.S. Cl. .................................... 424/251; 544/282
[58] Field of Search ....................... 544/282; 424/251

[56] References Cited

U.S. PATENT DOCUMENTS 3,585,198  6/1971  Meszaros et al. .................... 544/282
3,853,871 12/1974  Agata et al. .......................... 544/282
4,209,622  6/1980  Mészáros et al. ................... 544/282
4,234,586 11/1980  Hermecz et al. ................... 544/282

FOREIGN PATENT DOCUMENTS 1803785  6/1980  Fed. Rep. of Germany ...... 544/282

OTHER PUBLICATIONS

Katritzky et al, "Advances in Heterocyclic Chemistry," vol. 21, pp. 2-25, 1977, Academic Press, N.Y., Stedman's Medical Dictionary, 1976.
Chemical and Pharmaceutical Bulletin 21, 1305, 1973.
Justus Liebigs Ann. Chem. 103, 1973.
Chem. Commun. 805, 1966.

Lé Berre, A. et al, Bull. Soc. Chim. Fe., 9, pp. 3133-3138, 3139-3145, 3146-3151, (1969).
Burger: Medicinal Chemistry, 3rd Ed. pp. 1078-1082, (1970).
The Pharmacological Basis of Therapeutics Goodman et al, Fifth Edition, (New York 1975), pp. 326-327, 339 and 341.

Primary Examiner—Donald G. Daus
Assistant Examiner—Sharon A. Gibson
Attorney, Agent, or Firm—Karl F. Ross

[57] ABSTRACT

Chemical compounds having an effect on the circulatory system have the formulas

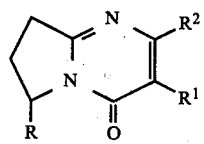
(I)

or

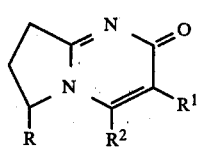
(II)

or a mixture thereof,
or a pharmaceutically suitable acid-addition salt or quaternary salt thereof, wherein
R is hydrogen or lower alkyl,
$R^1$ is lower alkyl, phenyl, carboxyl, lower alkoxycarbonyl, nitrile, carbamoyl or carbohydrazido,
$R^2$ is hydrogen or lower alkyl,
and wherein the formula I $R^2$ is hydrogen then $R^1$ is other than nitrile, alkoxycarbonyl or propyl.

2 Claims, No Drawings

3-SUBSTITUTED-TETRAHYDRO-PYRROLO[1,2-a]PYRIMIDINES AND PHARMACEUTICAL COMPOSITIONS

The invention relates to a process for the preparation of 3-substituted-tetrahydro-pyrrolo[1,2-a]pyrimidines are acid-addition and quaternary salts thereof and pharmaceutical compositions containing the same and new 3-substituted-tetrahydro-pyrrolo[1,2-a]pyrimidines and salts and quaternary salts thereof.

The preparation of pyrrolo[1,2-a]pyrimidines has not been studied thoroughly hereto. (Advances in Heterocyclic Chemistry Vol. 21, p. 3–25 (1977) edited by Academic Press) and only some references have been published concerning the preparation of 3-substituted-pyrrolo[1,2-a]pyrimidines. (Chem. Commun. 805 (1966); Khim. Geterosikl. Soedin. 3, 428, 1970 and 6, 765 1975; C. R. Hebd. Seances Acad. Sci., Ser C. 262, 365, 1966 and 265, 249, 1967; Bull. Soc. Chim. Fr. 9, 3133, 3139 and 3146, 1969. Justus Liebigs Ann. Chem. 103, 1973; Chem. Ber. 103, 1797, 1970 and 107, 270, 1974; Chem. Pharm. Bull. 21, 1305, 1973; and DE-Patent Specification No. 1 803 758 and Japanese Patent Specification No. 7 334 897 and HU-Patent Specification No. 167 676.)

According to HU-Patent Specification No. 167 676 2-methoxy-1-pyrroline is heated with diethyl-ethoxymethylene-malonate for 8 hours in the presence of ammonium acetate and the reaction mixture is processed in a complicated manner to give ethyl 4-oxo-4,6,7,8-tetrahydro-pyrrolo[1,2-a]pyrimidine with a yield of 7.1%. No melting point of the product is given, the product is characterized only by IR and PMR spectra.

According to Khim. Geterosikl. Soedin. 6, 765, 1975 ethyl-2-amino-4,5-dimethyl-thiophene-3-carboxylate is reacted with 2-methoxy-pyrroline in the presence of phosphoryl chloride and the obtained 2,3-dimethyl-4-oxo-5,6-tetramethylene-4H thieno[2,3-d]pyrimidine is desulphurated in an alcoholic solution wih Raney-nickel and thus 3-(1-methyl-propyl)-4-oxo-4,6,7,8-tetrahydropyrrolo[1,2-a]pyrimidine is obtained. In the complicated two-step synthesis the pyrrolo-pyrimidine derivative is obtained with a yield of 36.5%.

We have now found that by reacting 2-amino-pyrroline of the formula III

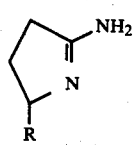

wherein

R is halogen or lower alkyl—containing two nucleophilic nitrogens— with an acrylic acid derivative of the formula IV

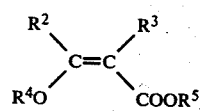

wherein $R^2$ is hydrogen or lower alkyl $R^3$ is lower alkyl, phenyl, cyano, or lower alkoxycarbonyl, $R^4$ is hydrogen, or lower alkyl, $R^5$ represents lower alkyl— a mixture of 4-oxo-pyrrolo[1,2-a]pyrimidine of the formula I

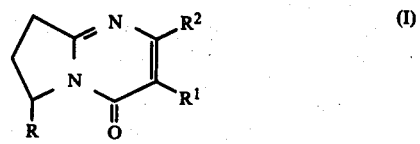

wherein $R^1$ is cyano or lower alkoxycarbonyl and of the formula II

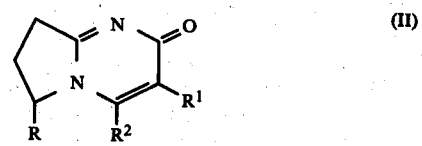

wherein $R^1$ is cyano or lower alkoxycarbonyl or lower alkyl or phenyl— is obtained, which may if desired be separated. If desired the obtained compound of the formula I or II containing alkoxy-carbonyl as $R^1$ may be (a) saponified to a carboxylic acid of the formula I or II containing carboxyl as $R^1$ or may be (b) reacted with ammonia to obtain an acid amide of the general formula I or II containing carbamoyl as $R^1$ or may be (c) reacted with hydrazine to obtain a compound of the formula I or II containing carbohydrazide as $R^1$. If desired a compound of the formula I or II containing carboxyl as $R^1$ may be esterified to give a compound of the formula I or II containing alkoxy-carbonyl as $R^1$. A compound of the formula I or II may be converted to an acid addition or quaternary salt thereof.

As starting material of the formula IV dialkyl ethoxymethylene malonate, alkyl ethoxy-methylene-cyano-acetate, alkyl ethoxy-methylene-cyano-acetate, alkyl 2-formyl-propionate, alkyl 2-formyl-phenyl-acetate, or ethyl 2-ethyl-acetoacetate are preferably used. As alkyl esters methyl, ethyl, isopropyl, n-propylesters are preferred.

The term "lower alkyl" as used herein stands for straight or branched alkyl containing 1 to 4 carbon atoms, such as methyl, ethyl, isopropyl, n-propyl, isobutyl, tert.butyl.

Compounds of the formula III are preferably reacted with the compounds of the formula IV in the presence of an inert solvent. As solvents preferably alcohols such as ethanol, methanol, esters such as ethyl acetate, ketones such as acetone, ethyl methyl ketone etc. aromatic hydrocarbons such as benzene, toluene, halogenated hydrocarbons such as chloroform, carbontetrachloride, chlorobenzene or a mixture thereof, may be employed.

The reaction is preferably carried out at −15° C. and 150° C. According to a preferred embodiment of the process of the invention to a solution of the compound of the formula III a solution of the compound of the formula IV is added. However the order of addition may be reversed.

When the solvent is distilled off a mixture of the compounds of the formulae I and II is obtained. The obtained mixture may be separated according to different solubility, basicity, or chromatographic behavior of the components.

The ester group in a given compound of the formula I or II—wherein R and $R^2$ are given above and $R^1$ stands for an ester group—may be converted to a carboxylic acid, carboxamide or carbohydrazide group by methods known per se.

When converting a compound of the formula I or II containing an ester as $R^1$ and R and $R^2$ are as given above, to carboxylic acid, the ester group may be hydrolyzed with dilute aqueous sodium hydroxide solution, followed by acidifying with hydrochloric acid, whereupon the obtained acid is precipitated and the acid is treated with aqueous or alcoholic ammonia solution or hydrazine hydrate and thus the carboxamide and carbohydrazide derivative can be obtained.

By treating a given compound of the formula I or II—wherein $R^1$ represents carboxamide—with a water removing agent such as phosphoryl chloride, a compound of the formula I or II is obtained wherein $R^1$ is cyano and R and $R^2$ are as given above. A compound of the formula I or II wherein $R^1$ stands for a carboxylic group may be converted to a compound of the formula I or II, wherein $R^1$ represents a lower alkoxycarbonyl group by methods known per se. The esterification may be conducted for example by using diazoalkanes, such as diazomethane or diazoethane or an alcohol-hydrogen chloride mixture. The compounds of the formula I or II wherein R, $R^1$ and $R^2$ are defined above may if desired be reacted with acids to give salts and with quaternizing agents to give quaternary salts. The base may be set free from the salts and if desired may be converted to other salts. Thus hydrochloric acid, hydrobromic acid, perchloric acid, acetic acid, salicylic acid salts and quaternary alkyl halide such as methyl iodide, dialkyl sulphate, such as dimethyl-sulphate, p-toluene-sulphonate, benzene sulphonate can be prepared.

Compounds of the formula IV are commercially available materials and compounds of the formula III may be easily prepared from pyrrolidin-2-one containing optionally lower alkyl in the 5-position, by reacting it first with an alkylating agent (e.g. diethyl sulphate) and obtaining O-alkyl iminoether which is then reacted with an agent setting free ammonia such as ammonium acetate, ammonium chloride, etc. to obtain a compound of the formula III.

The prepared compounds of the formula I or II wherein R, $R^1$, $R^2$ are as defined above, are mainly intermediate products for the preparation of valuable pharmaceutically active compounds but some representatives of the compounds may be employed as pharmaceutically active ingredients. Some representatives are starting materials in the synthesis of compounds acting favorably on the circulating system and some may be used as active ingredients of antianginal pharmaceutical compositions.

Compounds of the formula I and II as active ingredients can be employed in pharmaceutical compositions containing in addition to the active ingredient inert, non-toxic solid or liquid diluents, or carriers. The compositions can be administered in solid form such as tablets, capsules, dragées, or in liquid form such as in solution, suspension or emulsion.

Compounds of the formula I and II wherein R is hydrogen or lower alkyl, $R^1$ stands for lower alkyl, phenyl, carboxyl, lower alkoxycarbonyl, nitrile, carbamoyl, carbohydrazido and $R^2$ is hydrogen or lower alkyl, with the proviso, that if in the formula I $R^2$ is hydrogen then $R^1$ cannot be nitrile, alkoxycarbonyl or propyl, and pharmaceutically acceptable acid-addition salts and quaternary salts thereof, are new.

The further details of the invention are illustrated by the following Examples which serve merely for illustration and not for limitation.

EXAMPLE 1

50.5 g of 2-amino-pyrroline are dissolved in 600 ml. of ethanol and the solution is cooled to $-10°$ C., and added dropwise under stirring at $-10°$ C. to a solution of 127.8 g. of diethyl-ethoxy-methylene-malonate in 200 ml. of ethanol within 3 hours. The reaction mixture is then stirred for a further 1 hour at 0° C. and allowed to stand for 24 hours. The ethanol is distilled off at reduced pressure and the residual yellow oil, containing a mixture of ethyl-4-oxo-4,6,7,8-tetrahydro-pyrrolo[1,2-a]pyrimidine-3-carboxylate and ethyl 2-oxo-2,6,7,8-tetrahydro-pyrrolo[1,2-a]pyrimidino-3-carboxylate at a ratio of 4:1 is dissolved under boiling in 400 ml. benzene. The benzene solution is allowed to crystallize under cooling. The precipitated crystals are filtered. 22 g. (17%) of ethyl 2-oxo-2,6,7,8-tetrahydro-pyrrolo[1,2-a]pyrimidine-3-carboxylate are obtained, melting at 193° C. after recrystallization from ethanol.

Analysis for the formula: $C_{10}H_{12}N_2O_3$. Calculated: C, 57.69%; H, 5.76%; N, 13.46%. Found: C, 57.34%; H, 5.61%; N, 13.10%.

The benzene mother liquor is shaken out twice subsequently with 40 ml. of 5% W/V sodium hydrogen carbonate solution whereafter the combined aqueous solution is shaken back three times with 40 ml. of benzene. The combined benzene solution dried above anhydrous sodium sulphate is evaporated at reduced pressure and the residue is treated with 400 ml. of diethyl ether. The mixture is allowed to crystallize under cooling. The precipitated crystals are filtered. 60 g. (48%) of ethyl 4-oxo-4,6,7,8-tetrahydro-pyrrolo[1,2-a]pyrimidine-3-carboxylate are obtained, melting point: 59°–60° C.

Analysis for the formula $C_{10}H_{12}N_2O_3$. Calculated: C, 57.69%; H, 5.76%; N, 13.46%. Found: C, 57.81%; H, 5.57%; N, 13.48%.

If the ether mother liquor is saturated with hydrochloric acid gas further 22 g (15%) of ethyl 4-oxo-4,6,7,8-tetrahydro-pyrrolo[1,2-a]pyrimidine-3-carboxylate hydrochloride are obtained, melting at 182°–184° C.

Analysis for the formula: $C_{10}H_{13}N_2O_3Cl$. Calculated: C, 49.08%; H, 5.35%; N, 11.45%; Cl, 14.48%. Found: C, 49.23%; H, 5.61%; N, 11.36%; Cl, 14.36%.

EXAMPLE 2

One may proceed as described in Example 1 but 2-amino-pyrroline is replaced by 2-amino-5-methyl-pyrroline and the yellow oil obtained by evaporating the ethanolic solution and containing an about 2:1 mixture of ethyl 6-methyl-4-oxo-4,6,7,8-tetrahydro-pyrrolo[1,2-a]pyrimidine-3-carboxylate and ethyl 6-methyl-2-oxo-2,6,7,8-tetrahydro-pyrrolo[1,2-a]pyrimidine-3-carboxylate, is dissolved in benzene and the benzene solution is shaken out with 5% by W/V sodim hydrogen carbonate solution. The aqueous part is shaken back with benzene and shaken out with chloroform. The chloroform solution dried above anhydrous sodium sulphate is evaporated at reduced pressure. Ethyl 6-methyl-2-oxo-2,6,7,8-tetrahydro-pyrrolo[1,2-a]pyrimidine-3-carboxylate is obtained with a yield of 32.3% melting at 130° C. after recrystallization from a mixture of acetone and petrol ether.

Analysis for the formula: $C_{11}H_{14}N_2O_3$. Calculated: C, 59.45%; H, 6.35%; N, 12.61%. Found: C, 59.15%; H, 6.30%; N, 12.54%.

The benzene solution dried above anhydrous sodium sulphate is evaporated at reduced pressure. Ethyl 6-methyl-4-oxo-4,6,7,8-tetrahydro-pyrrolo[1,2-a]pyrimidine-3-carboxylate is obtained with a yield of 66% in the form of a pale yellow non-crystallizing oil.

Analysis for the formula: $C_{11}H_{14}N_2O_3$. Calculated: C, 59.45%; H, 6.35%; N, 12.61%. Found: C, 59.80%; H, 6.20%; N, 12.51%.

The oil mentioned above is dissolved in acetone and treated with hydrochloric acid gas and thus ethyl 6-methyl-4-oxo-4,6,7,8-tetrahydro-pyrrolo[1,2-a]pyrimidine-3-carboxylate-hydrochloride is obtained, melting at 161°–163° C.

Analysis for the formula $C_{11}H_{15}N_2O_3Cl$. Calculated: C, 51.07%; H, 5.84%; N, 10.83%; Cl, 13.70%. Found: C, 49.65%; H, 5.77%; N, 9.76%; Cl, 12.45%.

EXAMPLE 3

16.8 g. of 2-amino-pyrroline are dissolved in 140 ml. of ethanol and the solution is cooled to −5° C. and under stirring added dropwise to a solution of 33.8 g. of ethyl ethoxy-methylene-cyanoacetate in 250 ml. of ethanol. The reaction mixture is allowed to warm up to room temperature, and boiled for an hour. The reaction is then allowed to crystallize under cooling below 0° C. The precipitated crystals are filtered and thus 13.7 g. (42.5%) of 3-cyano-4-oxo-4,6,7,8-tetrahydro-pyrrolo[1,2-a]pyrimidine are obtained, melting at 119°–121° C. after recrystallization from ethanol.

Analysis for the formula $C_8H_7N_3O$. Calculated: C, 59.62%; H, 4.38%; N, 26.07%. Found: C, 59.49%; H, 4.24%; N, 26.04%.

EXAMPLE 4

One may proceed as described in Example 3 but 2-amino-pyrroline is replaced by 2-amino-5-methyl-pyrroline and thus 3-cyano-6-methyl-4-oxo-4,6,7,8-tetrahydro-pyrrolo[1,2-a]pyrimidine is obtained with a yield of 89%, melting at 148° C. after recrystallization from ethanol.

Analysis for the formula $C_9H_9N_3O$. Calculated: C, 61.70%; H, 5.18%; N, 23.98%. Found: C, 61.65%; H, 5.04%; N, 23.63%.

EXAMPLE 5

To a solution of 8.4 g. of 2-amino-pyrroline in 150 ml. of ethanol 1–2 drops of acetic acid and 13.01 g. of ethyl 2-formyl propionate are added and the reaction mixture is allowed to stand at room temperature for 24 hours. The reaction mixture is evaporated and the residue containing an about 1:1 mixture of 3-methyl-4-oxo-4,6,7,8-tetrahydro-pyrrolo[1,2-a]pyrimidine and 3-methyl-2-oxo-2,6,7,8-tetrahydro-pyrrolo[1,2-a]pyrimidine is boiled with 200 ml. of acetone and allowed to crystallize under cooling. The precipitated crystals are filtered. The acetone solution is evaporated and thus further crystals are obtained. Thus 6.7 g. (44.6%) of 3-methyl-2-oxo-2,6,7,8-tetrahydro-pyrrolo[1,2-a]pyrimidine are obtained, melting at 242° C.

Analysis for the formula $C_8H_{10}N_2O$. Calculated: C, 64.01%; H, 6.66%; N, 18.64%. Found: C, 63.85%; H, 6.54%; N, 18.73%.

After evaporating the acetone mother liquor 8.2 g. (54.6%) of 3-methyl-4-oxo-4,6,7,8-tetrahydro-pyrrolo[1,2-a]pyrimidine are obtained in the form of an oil which is slowly crystallizing upon standing. Melting point: 82° C.

Analysis for the formula $C_8H_{10}N_2O$. Calculated: C, 64.01%; H, 6.66%; N, 18.64%. Found: C, 63.50%; H, 6.71%; N, 18.52%.

EXAMPLE 6

One may proceed as described in Example 5 but 2-amino-pyrroline is replaced by 2-amino-5-methyl-pyrroline and thus 3,6-dimethyl-2-oxo-4,6,7,8-tetrahydro-pyrrolo[1,2-a]pyrimidine is obtained with a yield of 36%, melting at 150°–152° C. after recrystallization from methyl ethyl ketone.

Analysis for the formula $C_9H_{12}N_2O$. Calculated: C, 65.83%; H, 7.37%; N, 17.06%. Found: C, 65.54%; H, 7.42%; N, 17.15%.

3,6-dimethyl-4-oxo-4,6,7,8-tetrahydro-pyrrolo[1,2-a]pyrimidine is obtained with a yield of 42% from the acetone mother liquor in the form of yellow oil.

Analysis for the formula $C_9H_{12}N_2O$. Calculated: C, 65.83%; H, 7.37%; N, 17.06%. Found: C, 66.08%; H, 7.40%; N, 16.95%.

EXAMPLE 7

8.4 g. of 2-amino-pyrroline and 19.2 g. of ethyl 2-formyl-phenyl-acetate are heated in 150 ml. ethanol for 5 hours and the reaction mixture is evaporated. The residue is treated with petrol ether, the obtained crystals are filtered. 15.9 g. (75%) of a mixture of 3-phenyl-2-oxo-2,6,7,8-tetrahydro-pyrrolo[1,2-a]pyrimidine and 3-phenyl-4-oxo-4,6,7,8-tetrahydro-pyrrolo[1,2-a]pyrimidine are obtained, melting slowly between 98° to 120° C.

Analysis for the formula $C_{13}H_{12}N_2O$. Calculated: C, 73.57%; H, 5.70%; N, 13.20%. Found: C, 73.70%; H, 5.48%; N, 13.11%.

EXAMPLE 8

1 g. of a mixture of 3-phenyl-2-oxo-2,6,7,8-tetrahydro-pyrrolo[1,2-a]pyrimidine and 3-phenyl-4-oxo-4,6,7,8-tetrahydro-pyrrolo[1,2-a]pyrimidine obtained according to Example 7 is dissolved in benzene and applied to a silicagel column of a diameter of 1 cm. and consisting of 10 g. silicagel of particle size 0.063 to B 0.125 mm. Elution is first carried out with ethyl acetate. After evaporating the effluent ethyl acetate pure 3-phenyl-4-oxo-4,6,7,8-tetrahydro-pyrrolo[1,2-a]pyrimidine is obtained, melting at 172°–174° C.

Analysis for the formula $C_{13}H_{12}N_2O$. Calculated: C, 73.57%; H, 5.70%; N, 13.20%. Found: C, 73.41%; H, 5.62%; N, 13.28%.

Elution of the column is continued with methanol after removing 3-phenyl-4-oxo-4,6,7,8-tetrahydro-pyrrolo[1,2-a]pyrimidine followed by evaporation of the methanolic eluate and thus pure 3-phenyl-2-oxo-2,6,7,8-tetrahydro-pyrrolo[1,2-a]pyrimidine is obtained, melting at 200°–202° C.

Analysis for the formula $C_{13}H_{12}N_2O$. Calculated: C, 73.57%; H, 5.70%; N, 13.20%. Found: C, 73.60%; H, 5.81%; N, 13.07%.

EXAMPLE 9

10.4 g. of ethyl 4-oxo-4,6,7,8-tetrahydro-pyrrolo[1,2-a]pyrimidine-3-carboxylate are dissolved in 30 ml. of 30% by weight of ammonium hydroxide solution. The precipitated crystals are filtered after 2 hours. 8.7 g. of 3-carbamoyl-4-oxo-4,6,7,8-tetrahydro-pyrrolo[1,2-a]pyrimidine are obtained with a yield of 96.6%, which melts at 293° C. after recrystallization from dimethyl formamide.

Analysis for the formula $C_8H_9N_3O_2$. Calculated: C, 53.62%; H, 5.06%; N, 23.45%. Found: C, 53.47%; H, 5.12%; N, 23.23%.

EXAMPLE 10

One may proceed as described in Example 9, but as starting material ethyl 2-oxo-2,6,7,8-tetrahydro-pyrrolo[1,2-a]pyrimidine-3-carboxylate is used and 3-carbamoyl-2-oxo-2,6,7,8-tetrahydro-pyrrolo[1,2-a]pyrimidine is obtained with a yield of 88%, which melts at 277°–278° C. after recrystallization from n-butanol.

Analysis for the formula $C_8H_9N_3O_2$. Calculated: C, 53.62%; H, 5.06%; N, 23.45%. Found: C, 53.18%; H, 4.97%; N, 23.27%.

EXAMPLE 11

One may proceed as described in Example 9 but as starting material ethyl 6-methyl-4-oxo-4,6,7,8-tetrahydro-pyrrolo[1,2-a]pyrimidine-3-carboxylate is used and 3-carbamoyl-6-methyl-4-oxo-4,6,7,8-tetrahydro-pyrrolo[1,2-a]pyrimidine is obtained with a yield of 81% melting at 191° C.

Analysis for the formula $C_9H_{11}N_3O_2$. Calculated: C, 55.95%; H, 5.74%; N, 21.75%. Found: C, 56.03%; H, 5.84%; N, 21.70%.

EXAMPLE 12

One may proceed as described in Example 9 but as starting material ethyl 6-methyl-2-oxo-2,6,7,8-tetrahydro-pyrrolo[1,2-a]pyrimidine-3-carboxylate is used and 3-carbamoyl-6-methyl-2-oxo-2,6,7,8-tetrahydro-pyrrolo[1,2-a]pyrimidine is obtained with a yield of 76%, melting at 223° C.

Analysis for the formula: $C_9H_{11}N_2O_2$. Calculated: C, 55.95%; H, 5.74%; N, 21.75%. Found: C, 55.82%; H, 5.90%; N, 21.76%.

EXAMPLE 13

10.4 g. of ethyl 4-oxo-4,6,7,8-tetrahydro-pyrrolo[1,2-a]pyrimidine-3-carboxylate are dissolved in 50 ml. of a 5% by W/V sodium hydroxide solution and after two hours the pH of the reaction mixture is adjusted to 2.5 with 36% by W/V hydrochloric acid solution. The precipitated crystals are filtered and washed with a small amount of cold water. 6.0 g. (66.7%) of 4-oxo-4,6,7,8-tetrahydro-pyrrolo[1,2-a]pyrimidine-3-carboxylic acid are obtained melting at 146° to 148° C. (decomposition).

Analysis for the formula $C_8H_8N_2O_3$. Calculated: C, 53.23%; H, 4.48%; N, 15.55%. Found: C, 53.23%; H, 4.51%; N, 15.70.

EXAMPLE 14

One may proceed as described in Example 13 but as starting material ethyl 2-oxo-2,6,7,8-tetrahydro-pyrrolo[1,2-a]pyrimidine-3-carboxylate is used and 2-oxo-2,6,7,8-tetrahydro-pyrrolo[1,2-a]pyrimidine-3-carboxylic acid is obtained with a yield of 58%, melting under decomposition at 183° C.

Analysis for the formula $C_8H_8N_2O_3$. Calculated: C, 53.33%; H, 4.48%; N, 15.55%. Found: C, 53.40%; H, 4.42%; N, 15.55%.

EXAMPLE 15

One may proceed as disclosed in Example 13 but as starting material ethyl 6-methyl-4-oxo-4,6,7,8-tetrahydro-pyrrolo[1,2-a]pyrimidine-3-carboxylate is used and 6-methyl-4-oxo-4,6,7,8-tetrahydro-pyrrolo[1,2-a]pyrimidine-3-carboxylic acid is obtained with a yield of 56.5% melting under decomposition at 174° C.

Analysis for the formula $C_9H_{10}N_2O_3$. Calculated: C, 55.67%; H, 5.19%; N, 14.43%. Found: C, 55.71%; H, 5.15%; N, 14.52%.

EXAMPLE 16

One may proceed according to Example 13 but as starting material ethyl 6-methyl-2-oxo-2,6,7,8-tetrahydro-pyrrolo[1,2-a]pyrimidine-3-carboxylate is used and 6-methyl-2-oxo-2,6,7,8,9-tetrahydro-pyrrolo[1,2-a]pyrimidine-3-carboxylic acid is obtained with a yield of 43.5%, melting at 168° C. under decomposition.

Analysis for the formula $C_9H_{10}N_2O_3$. Calculated: C, 55.67%; H, 5.19%; N, 14.43%. Found: C, 55.80%; H, 5.19%; N, 14.40%.

EXAMPLE 17

2.08 g. of ethyl 4-oxo-4,6,7,8-tetrahydro-pyrrolo[1,2-a]pyrimidine-3-carboxylate is added to 10 ml. of 98% by weight of hydrazine hydrate and the mixture is allowed to stand for 1 hour at room temperature and the obtained crystals are filtered and washed with water. 1.5 g. (77.5%) of 4-oxo-4,6,7,8-tetrahydro-pyrrolo(1,2-a)pyrimidine-3-carbohydrazide is obtained, melting at 180°–181° C.

Analysis for the formula $C_8H_{10}N_4O_2$. Calculated: C, 49.48%; H, 5.19%; N, 28.85%. Found: C, 49.70%; H, 5.11%; N, 28.91%.

EXAMPLE 18

One may proceed as disclosed in Example 17 but as starting material ethyl 2-oxo-2,6,7,8-tetrahydro-pyrrolo[1,2-a]pyrimidine-3-carboxylate is used and 2-oxo-2,6,7,8-tetrahydro-pyrrolo[1,2-a]pyrimidine-3-carbohydrazide is obtained with a yield of 52% melting at 204°–206° C.

Analysis for the formula $C_8H_{10}N_4O_2$. Calculated: C, 49.48%; H, 5.19%; N, 28.85%. Found: C, 49.41%; H, 5.15%; N, 28.92%.

EXAMPLE 19

One may proceed as disclosed in Example 17 but as starting material ethyl 6-methyl-4-oxo-4,6,7,8-tetrahydro-pyrrolo[1,2-a]pyrimidine-3-carboxylate is used and 6-methyl-4-oxo-4,6,7,8-tetrahydro-pyrrolo[1,2-a]pyrimidine-3-carbohydrazide is obtained with a yield of 53%, melting point 136°–137° C.

Analysis for the formula $C_9H_{12}N_4O_2$. Calculated: C, 51.92%; H, 5.81%; N, 26.91%. Found: C, 52.15%; H, 5.90%; N, 26.75%.

EXAMPLE 20

One may proceed as disclosed in Example 17 but as starting material ethyl 6-methyl-2-oxo-2,6,7,8-tetrahydro-pyrrolo[1,2-a]pyrimidine-3-carboxylate is used and the reaction mixture is dissolved in ethanol after two hours standing followed by saturation with hydrochloric acid gas and the precipitated crystals are filtered. Thus 6-methyl-2-oxo-2,6,7,8-tetrahydro-pyrrolo[1,2-a]pyrimidine-3-carbohydrazide hydrochloride is obtained with a yield of 66.7% melting at 186° C.

Analysis for the formula $C_9H_{12}N_4O_2$. Calculated: C, 51.92%; H, 5.81%; N, 26.91%. Found: C, 51.86%; H, 5.80%; N, 27.08%.

EXAMPLE 21

2.08 g. of ethyl 4-oxo-4,6,7,8-tetrahydro-pyrrolo[1,2-a]pyrimidine-3-carboxylate are dissolved in 5 ml. of acetone and to the solution 2.5 ml. of methyl iodide are added. After 24 hours the precipitated crystals are filtered and washed with acetone. 2.61 g. (74%) of 3-ethoxycarbonyl-1-methyl-4-oxo-4,6,7,8-tetrahydro-pyrrolo[1,2-a]pyrimidinium iodide are obtained melting under decomposition at 212° C.

Analysis for the formula $C_{11}H_{15}N_2O_3I$. Calculated: C, 37.73%; H, 7.32%; N, 8.00%; I, 36.24%. Found: C, 37.68%; H, 4.39%; N, 7.95%; I, 35.6%.

EXAMPLE 22

One may proceed as described in Example 21 but as starting material ethyl 2-oxo-2,6,7,8-tetrahydro-pyrrolo[1,2-a]pyrimidine-3-carboxylate is used and the reaction is carried out in ethanol and thus 3-ethoxycarbonyl-6-methyl-2-oxo-2,6,7,8-tetrahydro-pyrrolo[1,2-a]pyrimidinium iodide is obtained with a yield of 58% melting at 223° C.

Analysis for the formula: $C_{11}H_{15}N_2O_3I$. Calculated: C, 37.73%; H, 4.32%; N, 8.00%; I, 36.24%. Found: C, 38.15%; H, 4.43%; N, 7.97%; I, 36.28%.

EXAMPLE 23

One may proceed according to Example 21 but as starting material ethyl 6-methyl-4-oxo-4,6,7,8-tetrahydro-pyrrolo[1,2-a]pyrimidine-3-carboxylate is used and the reaction is carried out in ethyl acetate and thus 3-ethoxycarbonyl-1,6-dimethyl-4-oxo-4,6,7,8-tetrahydro-pyrrolo[1,2-a]pyrimidinium iodide is obtained with a yield of 44% melting at 186°-187° C. under decomposition.

Analysis for the formula $C_{12}H_{17}N_2O_3I$. Calculated: C, 39.64%; H, 4.68%; N, 7.71%; I, 36.03%. Found: C, 39.65%; H, 4.90%; N, 7.72%; I, 36.18%.

EXAMPLE 24

One may proceed as disclosed in Example 21 but as starting material ethyl 6-methyl-2-oxo-2,6,7,8-tetrahydro-pyrrolo[1,2-a]pyrimidine-3-carboxylate is used and thus 3-ethoxycarbonyl-5,6-dimethyl-2-oxo-2,6,7,8-tetrahydro-pyrrolo[1,2-a]pyrimidinium-iodide is obtained with a yield of 82% melting at 208° C. under decomposition.

Analysis for the formula $C_{12}H_{17}N_2O_3I$. Calculated: C, 39.64%; H, 4.68%; N, 7.71%; I, 36.03%. Found: C, 39.70%; H, 4.52%; N, 7.80%; I, 36.30%.

EXAMPLE 25

To a solution of 5.37 g. of 3-carbamoyl-4-oxo-4,6,7,8-tetrahydro-pyrrolo[1,2-a]pyrimidine in 540 ml. of n-butanol 3.78 g. of dimethyl sulphate are added and the reaction mixture is stirred for 3 hours at 100° C. whereafter the solvent is distilled off. The residue is triturated with acetone and the obtained crystals are filtered. 3.7 g. (51%) highly hygroscopic 3-carbamoyl-1-methyl-4-oxo-4,6,7,8-tetrahydro-pyrrolo[1,2-a]pyrimidinium methyl sulphate are obtained melting at 190° C. under decomposition.

Analysis for the formula $C_{10}H_{15}N_3O_6S$. Calculated: C, 39.34%; H, 4.95%; N, 13.76%; S, 10.50%. Found: C, 39.44%; H, 5.03%; N, 13.92%; S, 10.41%.

EXAMPLE 26

To a solution of 1.93 g. of 3-carbamoyl-6-methyl-4-oxo-4,6,7,8-tetrahydro-pyrrolo[1,2-a]pyrimidine in 30 ml. of methanol 1.26 g. of dimethyl sulphate are added and the reaction mixture is heated for 1 hour and the mixture is then evaporated.

The residue is crystallized from acetone ether mixture. The obtained crystals are filtered. 2.7 g. (87%) of of highly hygroscopic 3-carbamoyl-1,6-dimethyl-4-oxo-4,6,7,8-tetrahydro-pyrrolo[1,2-a]pyrimidinium methyl sulphate are obtained melting at 110° C.

Analysis for the formula $C_{11}H_{17}N_3O_6S$ Calculated: C, 41.37%; H, 5.37%; N, 13.16%; S, 10.09%. Found: C, 41.45%; H, 5.41%; N, 13.15%; S, 9.86%.

EXAMPLE 27

42 g. of 2-amino-pyrroline are dissolved in 400 ml. of ethanol and at 0°-7° C. a solution of 108 g. of diethyl ethoxy-methylene-malonate in 200 ml. ethanol is added dropwise. After the addition is completed the mixture is stirred for 1 hour at 0° C., and allowed to stand for 12 hours at −5° C. The precipitated crystals are filtered. After evaporation of the alcohol the residue is boiled with 200 ml. of benzene. After cooling the insoluble crystals are filtered off. The filtered crystals are combined and recrystallized from ethanol. 50.3 g. (48.4%) ethyl 2-oxo-2,6,7,8-tetrahydro-pyrrolo[1,2-a]pyrimidine-3-carboxylate are obtained, melting at 193° C.

Analysis for the formula $C_{10}H_{12}N_2O_3$. Calculated: C, 52.6%; H, 5.26%; N, 12.28%. Found: C, 52.74%; H, 5.31%; N, 12.21%.

The benzene layer is shaken out twice with water. The aqueous layer is alkalized to pH=8 with sodium hydrogen carbonate and shaken out three times with 20 ml. of chloroform. The combined organic layer is dried above calcinated sodium sulphate and evaporated at reduced pressure. The obtained ethyl 4-oxo-4,6,7,8-tetrahydro-pyrrolo[1,2-a]pyrimidine-3-carboxylate is crystallized from ether. Yield: 40.5 g. (38.9%). M.p.: 59°-60° C.

Analysis for the formula $C_{10}H_{12}N_2O_3$. Calculated: C, 52.63%; H, 5.26%; N, 12.28%. Found: C, 52.78%; H, 5.30%; N, 12.19%.

EXAMPLE 28

0.84 g. of 2-amino-pyrroline and 1.5 g. of 2-ethylaceto-acetic ester are boiled in 10 ml. ethanol for 5 hours. Ethanol is evaporated. The residual oil is dissolved in 15 ml. chloroform and shaken out twice with 10 ml. of 5% sodium hydrogen carbonate. The chloroform layer is dried and evaporated at reduced pressure. The residual colourless oil is dissolved in acetone and dry hydrochloric acid gas is introduced into the solution. Upon adding ether white crystals are precipitating. 1.2 g. (56%) of 3-ethyl-2-methyl-4-oxo-4,6,7,8-tetrahydro-pyrrolo[1,2-a]pyrimidine hydrochloride is obtained.

Analysis for the formula $C_{10}H_{15}N_2OCl$.

Calculated: C, 55.94%; H, 7.04%; N, 13.04%; Cl, 16.51%. Found: C, 56.18%; H, 7.12%; N, 12.86%; Cl, 16.32%.

EXAMPLE 29

1.96 g. of 2-amino-5-methyl-pyrroline and 3.84 g. of ethyl-2-formyl-phenyl acetate are boiled in ethanol for 5 hours. The solvent is evaporated. The residual oil is processed according to Example 8. 1.08 g. (24%) 3-phenyl-6-methyl-4-oxo-4,6,7,8-tetrahydro-pyrrolo[1,2a]-pyrimidine is obtained melting at 118°–122° C. after recrystallization from aceton-ether mixture.

Analysis for the formula $C_{14}H_{14}N_2O$.

Calculated: C, 74.14%; H, 6.22%; N, 12.35%. Found: C, 74.15%; H, 6.21%; N, 12.48%.

1.5 g. (33%) of 3-phenyl-6-methyl-2-oxo-2,6,7,8-tetrahydro-pyrrolo[1,2-a]pyrimidine is also obtained melting at 178° C. after recrystallization from isopropanol.

Analysis for the formula $C_{14}H_{14}N_2O$. Calculated: C, 74.14%; H, 6.22%; N, 12.35%. Found: C, 73.89%; H, 6.15%; N, 12.33%.

Pharmacological Test Results

Antianginal activity of the compounds was determined in rats by inhibiting acute coronary insufficiency induced by intravenously administered vasopressin (Arch. Int. Pharmacodyn. 1966. 160, 147). Test-compounds were administered in an aqueous solution intravenously.

| Compound | i.v. dosage | protective activity % (rat) |
|---|---|---|
| Ethyl-4-oxo-4,6,7,8-tetrahydro-pyrrolo-[1,2-a]pyrimidine-3-carboxylate | 10 mg./kg. | 53.6% |
| Ethyl-2-oxo-2,6,7,8-tetrahydro-pyrrolo-[1,2-a]pyrimidine-3-carboxylate | 10 mg./kg. | 40.5% |
| 4-oxo-4,6,7,8-tetrahydro-pyrrolo[1,2-a]-pyrimidine-3-carbohydrazide | 10 mg./kg. | 55.0% |
| Papaverine | 2 mg./kg. | 36.9% |

We claim:

1. An antianginal method for treatment which comprises administering to an afflicted animal an effective amount of at least one compound of the formula (I) or (II)

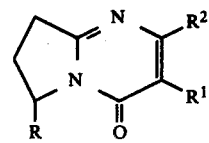  (I)

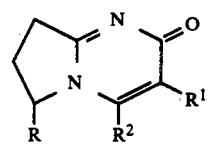  (II)

or a pharmaceutically acceptable acid addition or lower alkyl, phenyl, or lower alkyl-phenyl quaternary ammonium salt thereof, wherein
R is hydrogen or lower alkyl;
$R^1$ is carboxyl, lower alkoxycarbonyl, or carbohydrazido; and
$R^2$ is hydrogen or lower alkyl.

2. The antianginal method of treatment defined in claim 1 wherein the compound of the formula (I) or (II) administered is selected from the group consisting of:
ethyl-4-oxo-4,6,7,8-tetrahydro-pyrrolo[1,2-a]pyrimidine-3-carboxylate;
ethyl-2-oxo-2,6,7,8-tetrahydro-pyrrolo[(1,2)-a]pyrimidine-3-carboxylate; and
4-oxo-4,6,7,8-tetrahydro-pyrrolo[1,2-a]pyrimidine-3-carbohydrazide or a pharmaceutically acceptable acid addition or lower alkyl, phenyl or lower alkyl-phenyl quaternary ammonium salt thereof.

* * * * *